United States Patent
Kurita

(10) Patent No.: US 8,618,032 B2
(45) Date of Patent: Dec. 31, 2013

(54) POLYMER HAVING VISIBILITY IN MAGNETIC RESONANCE IMAGE AND SURFACE LUBRICITY AND MEDICAL DEVICE

(75) Inventor: Tomoka Kurita, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 147 days.

(21) Appl. No.: 12/442,065

(22) PCT Filed: Sep. 21, 2007

(86) PCT No.: PCT/JP2007/068367
§ 371 (c)(1),
(2), (4) Date: Mar. 19, 2009

(87) PCT Pub. No.: WO2008/035759
PCT Pub. Date: Mar. 27, 2008

(65) Prior Publication Data
US 2010/0019189 A1    Jan. 28, 2010

(30) Foreign Application Priority Data

Sep. 22, 2006 (JP) ................................. 2006-257318
Mar. 7, 2007 (JP) ................................. 2007-057488

(51) Int. Cl.
 *C10M 145/14* (2006.01)
 *C04B 35/04* (2006.01)
 *A61B 5/05* (2006.01)

(52) U.S. Cl.
USPC .......................... 508/469; 252/62.54; 600/410

(58) Field of Classification Search
USPC .......................... 508/469; 252/62.54; 600/410
See application file for complete search history.

(56) References Cited

U.S. PATENT DOCUMENTS

| 5,466,439 | A   | 11/1995 | Gibby et al. |
| 5,517,993 | A * | 5/1996  | Unger et al. ................. 600/410 |
| 6,060,040 | A   | 5/2000  | Tournier et al. |
| 6,361,759 | B1  | 3/2002  | Frayne et al. |
| 6,605,200 | B1  | 8/2003  | Mao et al. |

(Continued)

FOREIGN PATENT DOCUMENTS

JP    50-145432 A    11/1975
JP    2000-507962 A    6/2000

(Continued)

OTHER PUBLICATIONS

International Preliminary Report on Patentability/Written Opinion, mailed in corresponding PCT/JP2007/068367, Apr. 2, 2009, The International Bureau of WIPO, Geneva, CH.

(Continued)

*Primary Examiner* — Cephia D Toomer
*Assistant Examiner* — Vishal Vasisth
(74) *Attorney, Agent, or Firm* — Buchanan Ingersoll & Rooney PC

(57) ABSTRACT

Provided are a polymer which, when wetted, enables a medical apparatus for use in MRI diagnosis and therapy to be easily visible under MRI and, simultaneously, develops surface lubricity, and a medical apparatus coated with the polymer. The polymer including a copolymer composed of a substance for shortening relaxation time of a nuclear species capable of being detected by magnetic resonance, a moiety having a reactive group, and a moiety for developing lubricity is used to coat the medical apparatus, whereby excellent peel resistance, high lubricity, visibility under magnetic resonance, easy applicability, and high safety can be obtained.

13 Claims, 3 Drawing Sheets

(56) References Cited

U.S. PATENT DOCUMENTS

| | | |
|---|---|---|
| 6,896,874 B2 | 5/2005 | Li et al. |
| 2003/0100830 A1 | 5/2003 | Zhong et al. |
| 2004/0040840 A1* | 3/2004 | Mao et al. ............... 204/403.04 |
| 2004/0236215 A1* | 11/2004 | Mihara et al. .............. 600/434 |
| 2005/0271585 A1 | 12/2005 | Uzgiris et al. |

FOREIGN PATENT DOCUMENTS

| | | |
|---|---|---|
| JP | 2002-516132 A | 6/2002 |
| JP | 2003-514924 A | 4/2003 |
| JP | 2005-525176 A | 8/2005 |
| JP | 2005-239641 A | 9/2005 |
| JP | 2006-503594 A | 2/2006 |

OTHER PUBLICATIONS

"Development of an MR Marker for Interventional Radiology (IVR) Mainly Comprising Gd-DTPA Complex Polymer Composition," *Proceedings of the 32nd Meeting of the Japanese Society for Magnetic Resonance in Medicine*, 2004 (month unknown), p. 185, 181-22A; and English translation thereof.

* cited by examiner

POLYMER HAVING VISIBILITY IN MAGNETIC RESONANCE IMAGE AND SURFACE LUBRICITY AND MEDICAL DEVICE

This application is a 371 of PCT/JP2007/068367, filed Sep. 21, 2007.

TECHNICAL FIELD

The present invention relates to a polymer which, when wetted, enables a medical apparatus for use in MRI diagnosis or therapy to be MRI visible and, simultaneously, develops surface lubricity, and a medical apparatus coated with the polymer.

BACKGROUND ART

In recent years, clinical imaging diagnosis has been progressing remarkably, and the importance of diagnosis and therapy methods based on the use of magnetic resonance imaging (hereinafter referred to as MRI), radiography, ultrasonography, X-ray CT (computed tomography), scintigraphy, etc. has been increasing. Especially, the MRI enables sectional images taken in many arbitrary directions to be obtained with excellent tissue resolution while avoiding dose with radiations. In addition, the MRI provides functional information such as bloodstream, diffusion and temperature. Therefore, the usefulness of the MRI is highly evaluated in the imaging diagnosis field.

Attendant on the recent progress of the MRI-related hardware and imaging sequence, not only the imaging diagnosis but also clinical application of interventional MRI, in which diagnosis and therapeutic procedures are conducted under MRI observation, have been paid attention to. Researches of application of these procedures are under way, the application not being limited to non-vascular areas such as percutaneous puncture biopsy, various drainages, tumor cauterization, etc. but including vascular areas such as angioplasty, stent implanting technique, inferior aorta filter implanting technique, etc.

At present, the procedures relating to diagnosis and therapy in the vascular areas are conducted mainly under X-ray fluoroscopic observation. While only two-dimensional images can be obtained in X-ray fluoroscopy, three-dimensional images can be easily obtained in MRI. The three-dimensional images form information which is very useful in understanding complicated vascular anomalies, such as cerebral arteriovenous malformation and aneurysm. In addition, the various kinds of functional information that can be obtained by MRI cannot be obtained by X-ray fluoroscopy. Besides, the time taken for each of the diagnosis and therapeutic procedures in the vascular areas is about 3 hours on average, and may be 8 hours or longer in difficult cases. During the time required, the patient and the person involved in the medical work are continuously exposed to harmful radiations. In addition, the iodine-based contrast agent used in X-ray fluoroscopy is higher in harmfulness to the human body, as compared with the contrast agents used in MRI. Thus, conducting the diagnosis and therapy in the vascular areas under MRI observation has many merits, as compared with that under X-ray fluoroscopic observation.

However, most of the medical apparatuses used in the diagnosis and therapy in the vascular areas are formed of polymeric material, metal, ceramic or composite material thereof, which makes it impossible to obtain appropriate signals thereof in MRI and which is not visible under MRI. For safe and accurate procedures, therefore, it is desired to establish a technology for visualizing the medical apparatus under MRI.

As a technology for visualizing the medical apparatus under MRI, there have been proposed two types, i.e., an active tracking and a passive tracking. In the active tracking, one or more radio-frequency (RF) coils is incorporated into a medical apparatus such as a catheter, position is computed by a computer based on a magnetic resonance signal detected by the coil, and the computed result is displayed in the state of being superposed on a previously obtained anatomical image. According to this tracking, however, only the position where the coil is attached is visible, so that it is impossible to grasp the total image of the apparatus. Therefore, there is a limit to visualize a flexible apparatus such as catheter. Although incorporation of a multiple coil may be contemplated, it is unfavorable because it influences the mechanical properties of the catheter, probably spoiling the intrinsic functions of the catheter. Besides, heating of the apparatus due to an RF-induced current would also produce a problem.

On the other hand, in the passive tracking, a medical apparatus is visible based on a loss in a magnetic resonance signal. As an example of the passive tracking, there is a technology in which a nonmagnetic material not having a detectable magnetic resonance signal, such as plastic, is used to form the apparatus, and the apparatus is depicted as a no-signal area in an MRI image. This method is superior to the active tracking in that the entire image of the apparatus can be grasped, but the method has a problem in that the loss of signal relevant to the apparatus may be confused with the loss of signal due to air, flowing blood or the like. As another example of the passive system, there is a technology in which a material having a magnetic susceptibility different from those of the peripheral tissues is used to form the apparatus, and the apparatus is depicted by utilizing the distortion of image (artifact) of the periphery of the apparatus due to a magnetic susceptibility effect. However, there is a problem in that the magnetic susceptibility effect is dependent on the orientation of the apparatus relative to the static magnetic field in MRI, and the dimensions of the apparatus cannot be accurately visualized in the image obtained.

As a means for solving this problem, there has been devised a technology of visualizing a medical apparatus into a high signal in a magnetic resonance (hereinafter referred to as MR) image by utilizing the shortening effect on the relaxation time of proton arising from MR of a paramagnetic ion chelate complex. For example, there have been disclosed a method of chemically fixing a paramagnetic ion chelate complex onto a surface of a substrate (base material) constituting a medical apparatus (Patent Document 1), and a method of forming a coating on a surface of a medical apparatus (Patent Documents 3 and 4) by using a water-swellable polymer containing a paramagnetic ion chelate complex (Patent Document 2). By these systems, the whole part of a flexible apparatus such as catheter can be visualized in accurate dimensions.

Meanwhile, medical apparatuses for use in diagnosis and therapy in the vascular areas have to be provided with surface lubricity for reducing damage to the tissues and for enabling assured access of the apparatus to a target location. For this purpose, a method has been disclosed in which the coating film provided for generating a magnetic resistance signal is further coated with a film having surface lubricity (Patent Document 4, and Non-patent Document 1). However, this approach has problems in that the presence of multiple layers of coatings leads to much time required for development of visibility (in the case of Non-patent Document 1, visibility is developed after 15 hours from the moment of immersion in water), that the large coating thickness leads to high possibility of peeling, and that a multiple coating process are required.

As above-mentioned, interventional MRI is of great use in the vascular areas and, therefore, is expected to be advanced remarkably in the future. According to the prior art, however, no preferable method has been obtained that ensures that, when applied to diagnosis and therapy under MRI, the whole part of a medical apparatus can be visualized and, simultaneously, surface lubricity required in the procedures particularly in the vascular areas can be developed.

Patent Document 1: JP-T-2002-516132
Patent Document 2: Japanese Patent Laid-open No. 2005-239641
Patent Document 3: JP-T-2005-525176
Patent Document 4: JP-T-2006-503594
Non-patent Document 1: Proceedings of the 32nd Meeting of the Japanese Society for Magnetic Resonance in Medicine, 2004, p. 185, 181-22A

DISCLOSURE OF INVENTION

Technical Problem

The present invention has been made in consideration of the above-mentioned problems. Accordingly, it is an object of the present invention to provide a polymer which, when wetted, enables a medical apparatus used in diagnosis and therapy under MRI to be visible easily and, simultaneously, develops surface lubricity, and a medical apparatus coated with the polymer.

Technical Solution

The above object can be attained by the present invention described in the following (1) to (15).

(1) A polymer which, when wetted, develops MRI visibility and surface lubricity.

(2) The polymer according to (1) above, including a substance for shortening relaxation time of a nuclear species capable of being detected by magnetic resonance.

(3) The polymer according to (1) or (2) above, wherein the polymer includes a copolymer composed of a moiety having a reactive group and a moiety for developing lubricity.

(4) The polymer according to (3) above, wherein the substance for shortening the relaxation time is chemically bound to either one of the moiety having a reactive group and the moiety for developing lubricity.

(5) The polymer according to any of (2) to (4) above, wherein the substance for shortening the relaxation time includes an ion or particle which is paramagnetic or superparamagnetic.

(6) The polymer according to any of (3) to (5) above, wherein the moiety for developing lubricity is at least one selected from the group composed, as main constituent, of water-soluble monomers composed of: acrylamide and its derivatives; acrylic acid, methacrylic acid and their derivatives; and vinylpyrrolidone.

(7) The polymer according to any of (3) to (6) above, wherein the reactive group is at least one selected from the group composed of hydroxyl group, amino group, epoxy group, carboxyl group, acid chloride groups, aldehyde group, isocyanate group, and isothiocyanate group.

(8) The polymer according to any of (3) to (7) above, wherein the moiety having the reactive group is at least one selected from the group composed of a monomer having a reactive heterocyclic ring in its molecule, a monomer having an acid chloride in its molecule, and a monomer having an isocyanate group in its molecule.

(9) The polymer according to any of (3) to (8) above, wherein the copolymer constituting the polymer and the substance for shortening the relaxation time are covalently bound to each other either directly or through a linker molecule.

(10) The polymer according to any of (5) to (9) above, wherein said paramagnetic ion constitutes a paramagnetic ion chelate complex, and the ion is at least one selected from the group composed of chromium(III), manganese(II), iron(III), iron(II), cobalt(II), copper(II), nickel(II), praseodymium(III), neodymium(III), samarium(III), ytterbium(III), gadolinium (III), terbium(III), dysprosium(III), holmium(III), and erbium(III).

(11) The polymer according to any of (5) to (10), wherein a chelating agent constituting the paramagnetic ion chelate complex is at least one selected from the group composed of diethylenetriaminepentaacetic acid (DTPA), 1,4,7,10-tetraazacyclododecane-N,N',N'',N'''-tetraacetic acid (DOTA), 1,4,8,11-tetraazacyclotetradecane-N,N',N'',N'''-tetraacetic acid (TETA), diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(calboxylatomethyl)]-3,6,9-triazaundecanedioic acid (EOB-DTPA), benzyloxypropione tetraacetate (BOPTA), (4R)-4-[bis(carboxymethylamino)]-3,6,9-triazaundecanedioic acid (MS-325), 1,4,7-tris(carboxymethyl)-10-(2'-hydroxypropyl)-1,4,7,10-tetraazacyclododecane (HP-DO3A), DO3A-butrol, and derivatives thereof.

(12) The polymer according to any of (9) to (11) above, wherein the linker molecule is a bifunctional molecule.

(13) The polymer according to any of (9) to (12) above, wherein the linker molecule is at least one selected from the group composed of diamines, aminoalcohols, dialkylenetriamines, aminocarboxylic acids, lactams, diols, hydroxycarboxylic acids, dicarboxylic acids, diisocyanates, diisothiocyanates, aminoisocyanates, aminoisothiocyanates, hydroxylisocyanates, hydroxylisothiocyanates, carboxylisocyanates, and carboxylisothiocyanates.

(14) The polymer according to any of (3) to (13) above, wherein the copolymer is a block copolymer composed of a block having a reactive group and a block for developing lubricity.

(15) A medical apparatus wherein a substrate surface is coated with the polymer according to any of (1) to (14) above.

Advantageous Effects

As has been described above, the polymer according to the present invention produces a high signal under MRI and, when used to coat a medical apparatus, it ensures that the whole part of the medical apparatus is easily visible. Further, the polymer develops surface lubricity when wetted, and, when used to coat a medical apparatus applied to diagnosis and therapy particularly in the vascular areas, it reduces damages to the tissues and enables assured access of the apparatus to a target site. In addition, since MRI visibility and surface lubricity can be attained by use of the same polymer, a coating layer free of peeling of a lubricating layer or intricateness of production steps can be obtained.

BEST MODE FOR CARRYING OUT THE INVENTION

Now, the present invention will be described in detail below.

The present invention relates to a polymer which, when wetted, enables a medical apparatus for use in diagnosis or therapy under MRI to be visible and, simultaneously, develops surface lubricity for the medical apparatus, and to a medical apparatus coated with the polymer. Here, the polymer preferably includes a copolymer composed of a moiety having a reactive group and a moiety for developing lubricity, and more preferably is a polymer in which a substance for shortening relaxation time of a nuclear species capable of being detected by magnetic resonance (MR) is chemically bound to either one of the moiety having a reactive group and the moiety for developing lubricity.

In the present invention, the MRI visibility means that the medical apparatus in an MRI image can be visually confirmed distinctly from the image of the peripheral tissues. Besides, the surface lubricity in the present invention means a surface state of showing a low frictional resistance at the time of insertion, attachment and detachment, movement, implanting in a body, or the like when wetted with a body fluid such as saliva, digestive juice, blood, etc. or with an aqueous liquid such as physiological saline, water, etc. More specifically, the surface lubricity is measured by the method as follows.
<Evaluation Method for Surface Lubricity>

Measurement of frictional resistance can be carried out by the method as follows.

Figure 2:
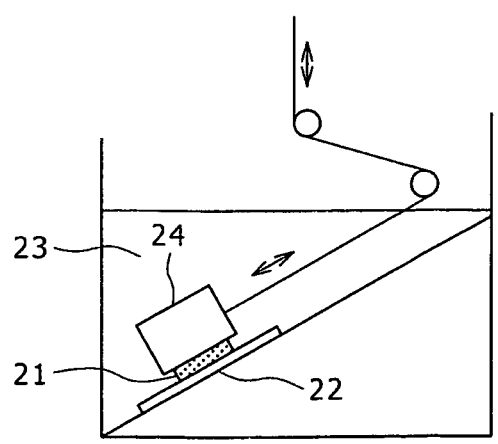
FIG. 2 is an overall diagram showing a test method for surface lubricity of a sheet-formed specimen according to the present invention.

A sheet 21 in which a surface similar to that of a medical apparatus is coated with a polymer according to the present invention is produced, and the frictional resistance on the sheet surface is measured by use of a jig as shown in FIG. 2. The sheet 21 (25 mm×25 mm) is fixed to a brass plate 22 by a adhesive tape, and this assembly is placed still on a plastic plate inclined at an inclination angle of 30° in water 23 for 10 minutes, thereby swelling the polymer sufficiently. Thereafter, a cylindrical brass weight 24 having a weight of 1 kg and a diameter of ϕ60 mm is calmly mounted on the sheet 21, and it is moved up and down over a width of 1 cm at a velocity of 1000 mm/min repeatedly 100 times by use of an autograph (AG-1kNIS, produced by Shimadzu Corp.), to measure frictional resistance. Here, as the frictional resistance, the difference between the value of frictional resistance in upward movement and the value of frictional resistance in downward movement is adopted. The final frictional resistance upon 100 runs of the test is calculated as an index of surface lubricity, and the change in frictional resistance (Δ frictional resistance) defined by the following formula (1) is calculated as a durable index of surface lubricity.

$$\Delta \text{ Frictional Resistance} = (\text{Final Frictional Resistance}) - (\text{Initial Frictional Resistance}) \quad (1)$$

Figure 3:
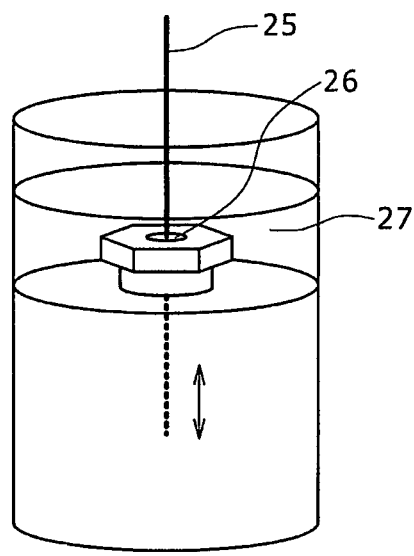
FIG. 3 is an overall diagram showing a test method for surface lubricity of a wire-formed specimen according to the present invention.

In addition, a medical wire 25 having a surface coated with a polymer according to the present invention is produced, and the frictional resistance on the wire 25 is measured by use of a jig as shown in FIG. 3. Specifically, the wire 25 is immersed in distilled water for 10 min, thereby swelling the polymer of the invention sufficiently. Then, the wire 25 is made to penetrate a silicone valve element 26 produced by forming a hole in the center of an HDD60 circular silicone sheet having a diameter of ϕ8 mm and a thickness of 1 mm by use of a 25 G injection needle (Terumo Injection Needle, produced by Terumo Corp.), and moved over a width of 20 mm at a velocity of 600 mm/min repeatedly 100 times by use of the autograph, to measure frictional resistance. The final frictional resistance upon 100 runs of test is calculated as an index of surface lubricity, and the change in frictional resistance (Δ frictional resistance) defined by the above formula (1) is calculated as a durable index of surface lubricity.

Simply, the surface lubricity can be evaluated by rubbing the relevant surface with a finger. The surface of the sheet coated with the polymer of the present invention is characterized by being slippery to the touch.
<MR-Detectable Nuclear Species and Substance Having Shortening Effect on Relaxation Time of MR-Detectable Nuclear Species>

The polymer in the present invention contains a substance having a shortening effect on the relaxation time of an MR-detectable nuclear species. This ensures that the intensity of an MR signal relevant to the nuclear species present in the polymer or in the vicinity of the polymer is changed so that the polymer and the medical apparatus coated with the polymer can be depicted distinctly from the image of the peripheral tissues.

The MR-detectable nuclear species in the present invention is not particularly limited, and is preferably proton (atomic nucleus of hydrogen). Examples of the proton include the protons of water molecules or hydroxyl groups present in the human body tissues, body fluids, etc. Examples of compounds including the hydroxyl group include hydroxyl group-containing compounds such as alkanols, for example, ethanol, glycerin (glycol), ethylene glycol, propylene glycol, polyethylene glycol, polypropylene glycol, well-known nontoxic hydroxylated compounds, and polyhydroxylated compounds. The protons present in the water molecules or hydroxyl groups present in the polymer of the present invention are also included in the above-mentioned nuclear species.

The substance having a shortening effect on the relaxation time of the MR-detectable nuclear species in the present invention is preferably an ion or particle which is paramagnetic or superparamagnetic. More preferable examples of the substance include paramagnetic ions, superparamegnetic particles, and paramagnetic ion chelate complexes in which the paramagnetic ion is coordinated with a chelating agent. The paramagnetic ions are preferable because they are lowered in toxicity when converted into paramagnetic ion chelate complexes, to be thereby enhanced in biocompatibility. The magnetic moment due to an unpaired electron in each of these substances causes a local change in the relaxation time of proton in the vicinity of the substance, whereby the intensity of the MR signal can be varied.

The paramagnetic ion is not particularly limited, and examples thereof include polyvalent metal ions of elements having atomic numbers of 21 to 29, 42, 44, and 58 to 70. Specifically, the paramagnetic ion is preferably selected from the group composed of chromium(III), manganese(II), iron (III), iron(II), cobalt(II), copper (II), nickel(II), praseodymium(III), neodymium(III), samarium(III), ytterbium(III), gadolinium(III), terbium(III), dysprosium(III), holmium (III), and erbium(III). Particularly, such ions as gadolinium (III), manganese(II), and iron(III) are more preferable in view of their strong magnetic moments. Further more preferable is gadolinium(III), which has the strongest magnetic moment.

The chelating agent constituting the above-mentioned paramagnetic ion chelate complex is not particularly limited, and is preferably selected from the group composed of diethylenetriaminepentaacetic acid (DTPA), 1,4,7,10-tetraazacyclododecane-N,N',N'',N'''-tetraacetic acid (DOTA), 1,4,8,11-tetraazacyclotetradecane-N,N',N'',N'''-tetraacetic acid (TETA), diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(calboxylatomethyl)]-3,6,9-triazaundecanedioic acid (EOB-DTPA), benzyloxypropione tetraacetate (BOPTA), (4R)-4-[bis(carboxymethylamino)]-3,6,9-triazaundecanedioic acid (MS-325), 1,4,7-tris(carboxymethyl)-10-(2'-hydroxypropyl)-1,4,7,10-tetraazacyclodecane (HP-DO3A), DO3A-butrol, and derivatives thereof. More preferable are DTPA, DOTA, TETA, DTPA-BMA, HP-DO3A, and further more preferable is DTPA.

In addition, the paramagnetic ion or the paramagnetic ion chelate complex may form a salt with an appropriate compound. Examples of such a salt include those of metals such as sodium, potassium, etc., organic bases such as ethanolamine, morpholine, meglumine (N-methylglucamine), etc., and amino acids such as arginine, ornithine, etc.

As the above-mentioned superparamagnetic particle, iron oxide particles can be used preferably. The iron oxide particles, preferably, are coated or modified with other organic compound, for the purpose of enhancing dispersibility, forming a bond with the substrate (base material) to be coated with the polymer, or forming a covalent bond with the reactive group of the polymer. Examples include iron oxide particles coated with dextran, which is well known as an MRI contrast agent, or the like. The particle diameter of the superparamagnetic particles is not particularly limited, and it is preferable to use particles having a diameter of 1 to 500 nm, more preferably 1 to 200 nm, and further preferably 1 to 100 nm.

The concentration of the paramagnetic or superparamagnetic ions or particles contained in the polymer according to the present invention depends on the static magnetic field strength and the magnetic gradient field strength of the MRI apparatus used for imaging, the imaging sequence and the like. Therefore, such a concentration as to promise a clear contrast between the tissues to be imaged and the polymer in the imaging sequence used is selected. As for the shortening effect of the paramagnetic or superparamagnetic ions or particles to the relaxation time of the protons present in the vicinity thereof, in general, the T1 relaxation time shortening effect is predominant when the concentration of the ions or particles is low, and the T2 relaxation time shortening effect is predominant when the concentration is high, with the effects being proportional to the intensity of the static magnetic field. The concentration of the paramagnetic or superparamagnetic ions or particles contained in the polymer can be determined, for example, by selecting an appropriate wavelength in ICP (inductively coupled plasma) emission spectrometry.

<Copolymer Composed of Moiety Having Reactive Group and Moiety for Developing Lubricity>

The polymer in the present invention is a polymer having MRI visibility and surface lubricity, and preferably includes a copolymer composed of a moiety having a reactive group and a moiety for developing lubricity. Incidentally, the moiety having a reactive group is composed of a monomer having in its molecule a reactive group which can be linked to a substrate constituting a medical apparatus or can be crosslinked by mutual linking, or a repetition of the monomer. In addition, the moiety for developing lubricity is composed of a hydrophilic monomer or a repetition of the hydrophilic monomer. Further, the copolymer is obtained by copolymerizing the monomer having a reactive group in its molecule or a repetition of the monomer with the hydrophilic monomer or a repetition of the hydrophilic monomer.

Examples of the reactive group include hydroxyl group, amino group, epoxy group, carboxyl group, acid chloride groups, aldehyde group, isocyanate group, and isothiocyanate group. Among these, preferred is the epoxy group from the viewpoint of reactivity.

Examples of the monomer having a reactive group in its molecule include a monomer of acrylic acid, methacrylic acid and their derivatives which have a reactive group in the molecule thereof. Specific examples of this monomer include monomers which have a reactive heterocyclic ring in the molecules thereof such as glycidyl acrylate, glycidyl methacrylate, etc., monomers having an acid chloride in the molecules thereof such as acryloyl chloride, methacryloyl chloride, etc., and monomers having an isocyanate group in the molecules thereof such as acryloyloxyethyl isocyanate, etc., of which two or more may be used in combination in such a range as to produce the effects of the present invention. Preferred ones of these monomers are glycidyl acrylate and glycidyl methacrylate, each of which has an epoxy group as the reactive group, the reaction of which is accelerated by heat or the like, and which are comparatively easy to handle.

Examples of the hydrophilic monomer include anionic, cationic, nonionic, and amphoteric hydrophilic monomers. Specific examples of the hydrophilic monomer include water-soluble monomers such as: acrylamide and its derivatives; acrylic acid, methacrylic acid, and their derivatives; maleic anhydride, maleic acid, and their derivatives; and vinylpyrrolidone. Preferable examples of the hydrophilic monomer include N-methylacrylamide, N,N-dimethylacrylamide, acrylamide, acryloylmorpholine, N,N-dimethylaminoethyl acrylate, 2-methacryloyloxyethylphosphorylcholine, 2-methacryloyloxyethyl-D-glycoside, 2-methacryloyloxyethyl-D-mannoside, vinylpyrrolidone, vinyl methyl ether and the like. These monomers are not limitative, and two or more of the hydrophilic monomers may be used in combination in such a range as to produce the effects of the present invention.

<Binding Between Copolymer and Substance Having Shortening Effect on Relaxation Time of MR-Detectable Nuclear Species>

In the polymer according to the present invention, either of the moiety having a reactive group and the moiety for developing lubricity which constitute the polymer and the substance having a shortening effect on the relaxation time of a MR-detectable nuclear species, preferably, are chemically bound to each other for the purpose of preventing elution of the substance into tissues or a body fluid.

The method for forming the chemical binding (chemical bond) is not particularly limited, and may be forming of a covalent bond or an ionic bond. A preferable example of the method is a method in which at least a part of the hydrophilic monomer or the monomer having a reactive group in its molecule in the copolymer and the above-mentioned chelating agent or the surface modifying group on the superparamagnetic particles or the like are covalently bound to each other either directly or through a linker molecule. The covalent bond can be formed by use of generally known chemical reactions. For example, the methods disclosed in Japanese Patent No. 3404787, PCT Patent Publication No. W006/

003731, etc. can be used to form the covalent bond. The case where a diamine is used as the linker molecule will now be described in detail below. Of the diamine, the amino group on one side is protected with a protective group such as tert-butoxycarbonyl group, benzyloxycarbonyl group, fluorenylmethoxycarbonyl group, etc., and the amino group on the other side is reacted with the carboxyl group of the above-mentioned substance or the acid anhydride thereof. Then, the protective group is eliminated by use of trifluoroacetic acid, palladium/carbon or the like, and the resulting amino group is reacted with the hydrophilic monomer or the monomer having a reactive group, thereby forming a covalent bond based on amino linkage. The linker molecule may be any polyfunctional molecule that has both a functional group which can form a covalent bond with the hydrophilic monomer or the monomer having a reactive group in its molecule and a functional group which can form a covalent bond with the functional group possessed by the above-mentioned substance. The linker molecule is preferably a bifunctional molecule. More preferable examples of the linker molecule include diamines, aminoalcohols, dialkylenetriamines, aminocarboxylic acids, lactams, diols, hydroxycarboxylic acids, dicarboxylic acids, diisocyanates, diisothiocyanates, aminoisocyanates, aminoisothiocyanates, hydroxylisocyanates, hydroxylisothiocyanates, carboxylisocyanates, and carboxylisothiocyanates.

<Kinds of Copolymer>

The above-mentioned copolymer includes random, block and graft copolymers and the like. From the viewpoints of high water absorptivity and high lubricity, however, the water swellable polymer in the present invention is preferably a block copolymer such as a diblock copolymer and a triblock copolymer. More preferably, the copolymer is a block copolymer in which two kinds of blocks, i.e., one block composed of a repetition of the monomer having a reactive group in its molecule and one block composed of a repetition of the hydrophilic monomer are linked to each other.

PREFERABLE MODES OF THE INVENTION

Figure 1:
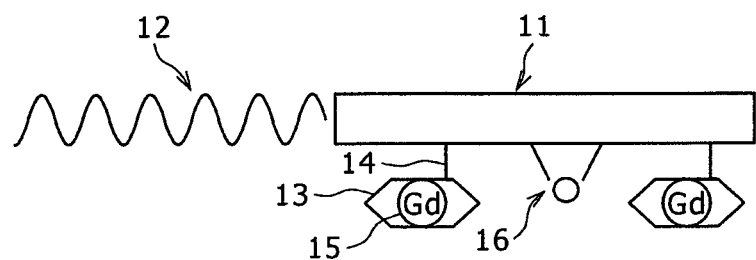
FIG. 1 shows schematic diagrams showing preferable two different modes of carrying out the polymer according to the present invention.

FIG. 1 is a schematic diagram illustrating preferable two different modes of the polymer according to the present invention. Polymer A of the present invention represents an example in which glycidyl methacrylate (GMA) is used as the monomer constituting the moiety 11 having a reactive group, while dimethylacrylamide (DMAA) is used as the monomer constituting the moiety 12 for developing lubricity, and the substance for shortening the relaxation time is bound to the side of the moiety having the reactive group. One example of the method for preparing Polymer A is as follows. First, a polymerization initiator is added to the GMA monomer and polymerization is carried out, to obtain poly-GMA having a radical (peroxide group) in its molecule. Subsequently, polymerization of the DMAA monomer is carried out using the poly-GMA as a polymerization initiator, to obtain a block copolymer in which the two kinds of homopolymers, i.e., a GMA homopolymer and a DMAA homopolymer are linked. Separately, DTPA-mono-2-aminoethylamide in which the chelating agent 13 is diethylenetriaminepentaacetic acid (DTPA) and the linker molecule 14 is 1,2-diaminoethane is synthesized. Then, the linker molecule-bonded chelating agent is covalently bound to the reactive group 16 (here, the epoxy group) in the block copolymer. In this case, all the reactive groups 16 are not reacted; instead, part of the reactive groups 16 are left intact for linkage to the substrate constituting a medical apparatus or for mutual crosslinking of the reactive groups 16. Further, gadolinium as a paramagnetic ion 15 is coordinated in the chelate, to obtain the objective polymer.

Polymer B of the present invention represents an example in which GMA is used as the monomer constituting the moiety 11 having a reactive group, while DMAA and 2-hydroxyethyl methacrylate (HEMA) are used as the monomers constituting the moiety 12 for developing lubricity, and the substance for shortening the relaxation time is bound to the moiety 12 for developing lubricity. One example of the method for preparing Polymer B is as follows. First, a polymerization initiator is added to the GMA monomer and polymerization is carried out, to obtain poly-GMA having a radical (the peroxide group) in its molecule. Subsequently, using the poly-GMA as a polymerization initiator, DMAA and HEMA to which DTPA as the chelating agent 13 has been preliminarily covalently bound are simultaneously added to the poly-GMA, and polymerization is carried out. As a result, a block copolymer is obtained in which two kinds of polymers, i.e., a GMA homopolymer and a random polymer of the DMAA and the HEMA preliminarily covalently bound to DTPA are linked. Further, gadolinium as the paramagnetic ion 15 is coordinated in the chelate, to obtain the objective polymer.

In this manner, the polymer of the present invention includes the block copolymer in which one block composed of a repetition of the monomer having a reactive group in its molecule (the moiety having a reactive group) and one block composed of a repetition of the hydrophilic monomer (the moiety for developing lubricity) are linked to each other. As a result of this configuration, the following effects can be obtained. (1) Peeling of a lubricating layer is obviated, and permanent lubricity can be obtained. (2) It is considered that, when a medical apparatus is coated with this polymer, the moiety having the reactive group which is comparatively low in hydrophilicity is disposed on the side of the medical apparatus whereas the moiety for developing lubricity which is comparatively high in hydrophilicity is exposed to the surface, so that higher lubricity can be obtained as compared with the case of using a random polymer. (3) The coating with one kind of polymer and the monolayer coating structure promise a higher visibility under MRI, as compared with the case of a multilayer coating. (4) The moiety having the reactive group for linkage to the substrate constituting a medical apparatus or for mutual crosslinking of the reactive groups, the moiety showing lubricity, and the moiety providing visibility are contained in one polymer, so that there is no need for a special primer solution, and the medical apparatus can be coated with the polymer by a single coating process, whereby excellent operability and safety are ensured. (5) Since the substance for shortening the relaxation time of the MR-detectable nuclear species is covalently bound to the copolymer, the paramagnetic ions or the like would not flow out in a short time, which ensures excellent safety. (6) Besides, the ratio of the moiety 11 (GMA) having the reactive group to the moiety 12 (DMAA, or DMAA and HEMA) for developing lubricity in the block copolymer is preferably in the range from 1:1 to 1:49, more preferably from 1:3 to 1:19. If the proportion of the moiety exhibiting lubricity is too high, the polymer would be dissolved in water. The just-mentioned range of the ratio is determined for obviating this problem and taking into account the harmony between the lubricity and the visibility under MRI.

<Method for Preparation of Polymer>

The sequence in which the covalent bonds are formed respectively between the moiety having the reactive group constituting the polymer, the substance having the shortening effect on the relaxation time of the MR-detectable nuclear species and the linker molecule optionally introduced as required is not particularly limited to that in the above-mentioned method. In addition, the coordination of the paramagnetic ion may be carried out at any stage in the preparation of the polymer. The coordination of the paramagnetic ion can be carried out, for example, by dissolving the compound including the chelating agent and a salt of the paramagnetic ion in a solvent, followed by stirring.

<Others>

The polymer in the present invention may be subjected to a crosslinking treatment, for the purpose of enhancing the durability of the polymer or controlling the lubricity thereof. As a method for the crosslinking treatment, known methods can be applied. Examples of the applicable method include a method in which active radicals are generated by light, heat, radiations or the like, a method in which a polymerizable polyfunctional monomer is added, a method in which a polyfunctional crosslinking agent is applied, and a method in which functional groups in each molecule are crosslinked with each other by use of a catalyst. In the case of a water-swellable polymer containing highly reactive functional groups such as epoxy groups, the polymer can be easily crosslinked through polymerization among the epoxy groups or by use of a diamino compound, a dihydroxy compound, a dialdehyde compound or the like.

On the polymer in the present invention, a physiologically active substance or a drug may be loaded, for enhancing the diagnostic or therapeutic effect or for sustained release. Specific examples of such physiologically active substances and drugs include carcinostatic, antibiotic, physiologically active polypeptides, antipyretic, sedative, immunoactivable agent, anti-inflammatory agent, antitussive, antiepileptic, antihistamic agent, hypotensive diuretic, antidiabetic drug, muscle relaxant, antineoplastic agent, antidepressant, antiallergic agent, cardiac, antiarrhythmic agent, vasodialator, anticoagulant, narcotic antagonist, styptic, antitubercular agent, hormone preparation and the like.

<Medical Apparatus Coated with Polymer Having MRI Visibility and Surface Lubricity, and Method of Producing the Same>

The substrate (base material) of the medical apparatus according to the present invention is not particularly limited. Examples of the substrate include synthetic and natural polymers, metals, ceramics and the like. Examples of the synthetic polymers include: various resin materials such as polyolefins such as polyethylene, polypropylene, polybutadiene, etc., polyvinyl chloride, polyurethane, ethylene-vinyl acetate copolymer, polyesters such as polyethylene terephthalate, polybutylene terephthalate, etc., polyamide, polyether-polyamide, polyester-polyamide, soft polyvinyl chloride, ABS resin, AS resin, fluororesins such as polytetrafluoroethylene, etc., shape memory resins, etc.; various thermoplastic elastomers based on styrene, polyolefin, polyurethane, polyester, polyamide, polybutadiene, trans-polyisoprene, fluoro-rubber, chlorinated polyethylene, or the like; and combinations of two or more of these (polymer alloys, polymer blends, laminates, etc.). These substrates (base materials) may each be subjected to a surface treatment for the purpose of enhancing affinity for the polymer with which it is coated or for the purpose of forming covalent bonds.

As the method for coating a medical apparatus with the polymer in the present invention, well-known coating methods can be used. For example, the whole part or a part of a medical apparatus to be coated is immersed in a solution, dispersion or emulsion of the polymer, followed by drying to remove the solvent, whereby a layer composed of the polymer can be formed on a surface of the substrate (base material) constituting the medical apparatus. Or, a solution, dispersion or emulsion of the polymer may be sprayed onto a surface of the substrate, followed by drying. In this case, the substrate surface and the polymer may react with each other, to form covalent bonds. Particularly, Japanese Patent No. 3580843 discloses a method in which a surface of a substrate containing as a constituent a synthetic polymer having an acid anhydride is coated with a polymer having a functional group capable of reacting with the acid anhydride, followed by a heating treatment at a temperature of not less than 30° C. to form a coating layer. In addition, Japanese Patent No. 3631781 discloses a method wherein a polymer is dissolved in a solvent with which a polymeric substrate constituting a medical apparatus not having a reactive group capable of reacting with the polymer is swelled at a swelling ratio of 1 to 100%, to prepare a solution of the polymer, the polymeric substrate is immersed in the thus prepared solution so as to be swelled, and, further, the polymeric substrate surface and the polymer are mutually crosslinked or polymerized, whereby an interpenetrating network structure is formed between the polymeric substrate surface and the polymer. When the coating is carried out by use of any of these methods, the polymer is firmly fixed to the surface of the substrate (base material) constituting the medical apparatus, and a polymer layer excellent in peel resistance can be obtained in a preferable manner. The present invention includes formation of a coating layer composed of the polymer, naturally inclusive of the above mentioned specific examples.

The polymer according to the present invention can be used as a coating material for medical apparatuses in preferable manner. The medical apparatus here means an apparatus required to perform objective procedures in medical activities. Examples of the medical apparatus required to have MRI visibility and surface lubricity, preferably, include catheters and guide wires to be used, particularly, in blood vessels. In addition to these examples, examples of the medical apparatus further include the following.

(1) Catheters to be inserted through the mouth or nose into a digestive tract or left indwelling there, such as stomach tube catheter, nutrient catheter, and transluminal nutrition (ED) tube.

(2) Catheters to be inserted through the mouth or nose into the respiratory tract or an organ or left indwelling there, such as oxygen catheter, oxygen cannula, tube and cuff of endotracheal tube, tube and cuff of tracheotomy tube, and endotracheal aspirating catheter.

(3) Catheters to be inserted into the urethra or the ureter or left indwelling there, such as urethral catheter, urine-conducting catheter, and catheter and balloon of balloon catheter.

(4) Catheters to be inserted into various lumens, organs and tissues or left indwelling there, such as aspiratory catheter, drainage catheter, and rectal catheter.

(5) Indwelling needles as well as catheters to be inserted into blood vessels or left indwelling there, such as IVH catheter, thermodilutional catheter, angiographic catheter, vascular dilation catheter, and dilator or introducer; and guide wires, stylets, etc. for these catheters.

(6) Inspection apparatuses, therapeutic apparatuses, etc. to be inserted into various organs.

(7) Stents as well as artificial blood vessels, artificial organs, artificial bronchia, etc.

(8) Medical apparatuses (artificial heart, artificial lung, artificial kidney) for extracorporeal circulatory therapy, and circuitry therefor.

Figure 4:
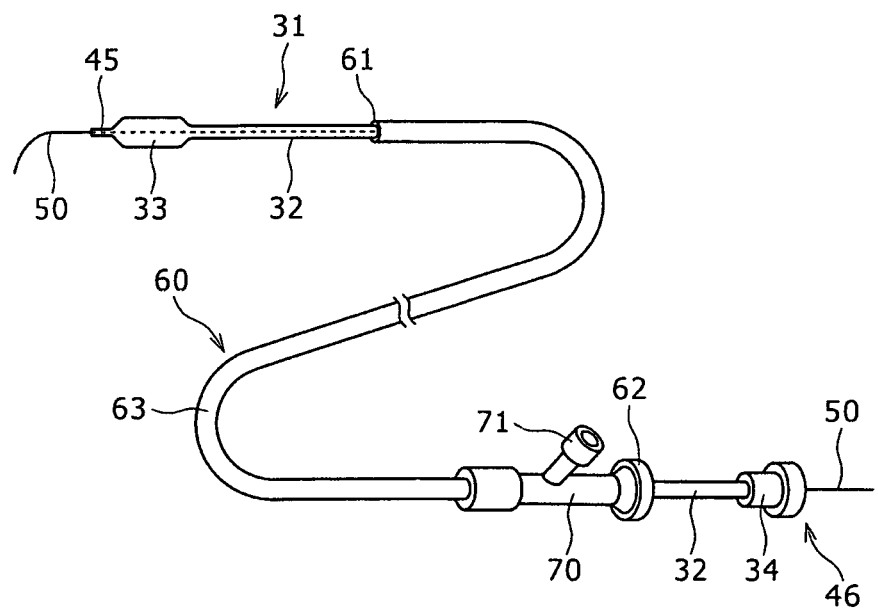
FIG. 4 is a perspective view of a vascular dilation catheter according to an embodiment of the present invention.
Figure 5:
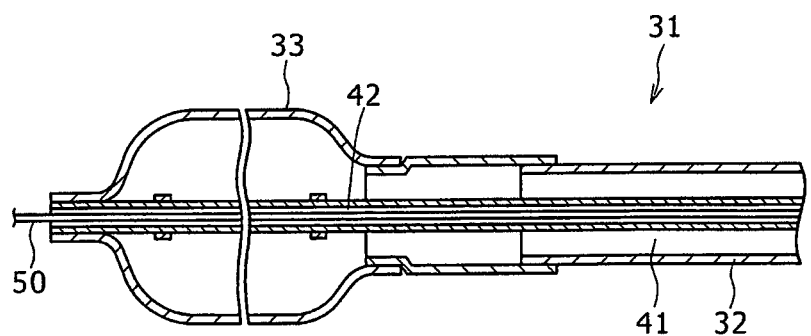
FIG. 5 is a longitudinal sectional view of the vicinity of a distal portion of the vascular dilation catheter according to the embodiment of the present invention.

FIG. 4 is a perspective view of a vascular dilation catheter according to an embodiment of the present invention, and FIG. 5 is a longitudinal sectional view of the vicinity of a distal portion of the catheter shown in FIG. 4. As shown in FIG. 4, the catheter 31 has a distal end 45 and a proximal end 46, with a catheter body 32 extending therebetween. Further, the catheter 31 includes the catheter body 32, a balloon 33 which is attached to a distal portion of the catheter body and which can be dilated and contracted, and a hub 34 attached to a proximal portion of the catheter body. As shown in the longitudinal sectional view of FIG. 5, there are provided a guide wire lumen 42 and a balloon lumen 41 which penetrate the catheter body 32 over the range from the distal end 45 to the proximal end 46. A guide wire 50 is inserted in the guide wire lumen 42.

The guide wire 50 is a filamentous member having a distal end and a proximal end. The length of the guide wire 50 is not less than the overall length of the catheter 31.

The catheter 31 and the guide wire 50 as above are used in the state of being inserted in a guiding catheter 60. The guiding catheter 60 has a distal end 61 and a proximal end 62, with a guiding catheter body 63 extending therebetween. A Y-connector 70 is attached to the proximal side of the guiding catheter. The Y-connector 70 is provided therein with a lumen along the longitudinal direction thereof, and this lumen communicates with the lumen of the guiding catheter 60. The catheter 31 and the guide wire 50 are passed through the lumens of the guiding catheter 60 and the Y-connector 70, to protrude from the proximal end of the Y-connector 70. In addition, the Y-connector 70 is provided with a tubular branch portion 71.

The catheter 31 is used in the case of application to PTCA (Percutaneous Transluminal Coronary Angioplasty) or the like. The guiding catheter 60 with a guide wire (not shown) inserted therein is inserted into an artery through a sheath of a catheter introducer, by the Seldinger technique. Then, while being preceded by the guide wire, the guiding catheter 60 is advanced, retracted and rotated repeatedly so that a distal portion thereof is brought to an entrance portion of a coronary artery, to be left indwelling there. After the guide wire is pulled off, the catheter 31 with the guide wire 50 inserted therein is advanced in the distal direction along the lumen of the guiding catheter 60 so that a distal portion of the catheter is protruded from the opening at the distal end 61 of the guiding catheter 60. After the distal portion of the catheter has arrived at the inside of the coronary artery, the guide wire 50 is advanced while rotating it if necessary, whereby a distal portion thereof is passed through a stenosis portion of the coronary artery, which is the target site. After the distal end of the guide wire 50 has passed through the coronary artery stenosis portion, the advancing of the guide wire 50 is stopped, then the catheter 31 is slowly advanced along the guide wire 50, and the balloon 33 is located in the coronary artery stenosis portion. Next, a working fluid is injected through the hub 34, and is supplied into the balloon 33 through the lumen of the hub 34 and a balloon lumen 41 so that the balloon 33 is dilated. By this operation, the stenosis portion of the coronary artery is dilated.

When the catheter in which a substrate surface is coated with a polymer having MRI visibility and surface lubricity according to the present invention is used, the above-mentioned operations can be carried out easily and safely. That portion of the catheter which is coated may be either the whole part of the surface of the catheter or a part of the surface. Particularly, it is preferable to coat with the polymer of the present invention that portion of the surface of the guiding catheter 60 which is on the distal side of the Y-connector 70, that distal portion of the catheter which includes the balloon 33, that overall surface of the guide wire 50, that distal portion of the surface of the catheter lumen in which the guide wire 50 is inserted, or the like.

A preferable portion to be treated with the polymer of the present invention can also be determined by a method in which appropriate blood vessel models and body lumen models are preliminarily fabricated, a variety of samples varied in the position and length of the portion to be treated and in the level of slidability upon swelling with water and the like are prepared, and the samples are compared with one another.

Furthermore, while the polymer according to the present invention is composed of a polymer which develops MRI visibility and surface lubricity, a portion coated with a substance for developing only surface lubricity according to the prior art and a portion coated with the polymer according to the present invention may be used separately. For example, a configuration may be adopted in which only distal portions of a guide wire and a catheter are coated with the polymer of the present invention so that the portions develop both functions of providing MRI visibility and surface lubricity, whereas the other portions of the guide wire and the catheter as well as the whole part of a guiding catheter are coated with the substance for developing only surface lubricity.

Now, the present invention will be described specifically below by showing examples, but the invention is not limited to the examples. Here, Examples 1 to 9 correspond to A of FIG. 1, and Example 10 corresponds to B of FIG. 1.

EXAMPLES

Example 1

Synthesis of Polymer Having MRI Visibility and Surface Lubricity

<1> Synthesis of Block Copolymer

A block copolymer having dimethylacrylamide (DMAA) as the portion 12 for developing lubricity and glycidyl methacrylate (GMA) as the portion 11 having a reactive group was synthesized.

After 17 g of triethyleneglycol (produced by Tokyo Chemical Industry Co., Ltd.) was added dropwise to 55 g of sebasic acid dichloride (produced by Tokyo Chemical Industry Co., Ltd.) at 50° C., hydrochloric acid was removed at a reduced pressure at 50° C. for 3 hours, to obtain an oligoester. An admixture obtained by adding 6.1 g of methyl ethyl ketone (produced by Nacalai Tesque, Inc.) to 65 g of the oligoester obtained above was dropped into a solution containing 21 g of sodium hydroxide (Sodium Hydroxide (granular), produced by Kanto Chemical Co., Ltd.), 14 g of 31% hydrogen peroxide (Hydrogen Peroxide (oxygenated water), produced by Kanto Chemical Co., Ltd.) and 0.6 g of surfactant dioctyl phosphate (produced by Aldrich) in 500 g of water, and reaction was allowed at −5° C. for 1 hour. The reaction product was washed with water and with methanol repeatedly, followed by drying, to obtain a polyperoxide (PPO) having a plurality of peroxide groups in its molecule. Subsequently, using 10 g of the PPO as a polymerization initiator and 400 g of 1,4-dioxane (produced by Nacalai Tesque, Inc.) as a solvent, 90 g of GMA (produced by Wako Pure Chemical Industries, Ltd.) was subjected to polymerization with stirring in a nitrogen atmosphere at 80° C. for 2 hours. The reaction product was purified using n-hexane (produced by Kokusan Chemical Co., Ltd.) as a poor solvent and tetrahydrofuran (produced by Kanto Chemical Co., Ltd.) as a good solvent, to obtain a poly-GMA having peroxide groups in its molecule. Subsequently, using 45 g of the poly-GMA as a polymerization initiator and 2.6 kg of chlorobenzene (produced by Wako Pure Chemical Industries, Ltd.) as a solvent, 330 g of DMAA was subjected to polymerization reaction by heating at 80° C. for 5 hours. After the reaction, the product was purified using n-hexane as a poor solvent and tetrahydrofuran as a good solvent, to obtain a block copolymer having epoxy groups in its molecule and developing lubricity when wetted. An analysis by $^1$H-NMR (UnityPlus400, produced by Varian) confirmed the presence of the epoxy group in the molecule of the block copolymer.

<2> Synthesis of Linker Molecule-Bonded Chelating Agent

DTPA-mono-2-aminoethylamide having DTPA as a chelating agent and 1,2-diaminoethane as a linker molecule was synthesized.

After 35.7 g (100 mM) of diethylenetriaminepentaacetic acid dianhydride (DTPAda, produced by Aldrich) was added to 500 ml of anhydrous dimethylformamide (anhydrous DMF, produced by Wako Pure Chemical Industries, Ltd.) and the admixture was heated at 80° C. to effect dissolution, 1.80 ml (100 mM) of distilled water was added dropwise to the solution, followed by stirring further for 1 hour. To the thus obtained solution, a solution prepared by dissolving 16.0 g (100 mM) of N-(tert-butoxycarbonyl)-1,2-diaminoethane (produced by Tokyo Chemical Industries Co., Ltd.) in 120 ml of anhydrous DMF was added dropwise, followed by stirring further for 2 hours at the above-mentioned temperature. The reaction mixture was added dropwise to diethyl ether (produced by Kokusan Chemical Co., Ltd.) to precipitate the reaction product, and the product was collected by suction filtration, and was dried under a reduced pressure, to obtain 56.4 g of a white powder. The powder was isolated and purified by chromatography using chromatography-grade silica gel (ChromatorexODS DM1020T, produced by Fuji Silysia Chemical Ltd.) and using water/acetonitrile (produced by Kanto Chemical Co., Ltd.) mixed solvent (8/2, v/v) as a developing solvent, to obtain DTPA-mono-2-(N-tert-butoxycarbonylamino)ethylamide.

Subsequently, 170 ml of trifluoroacetic acid (produced by Wako Pure Chemical Industries, Ltd.) was added to 16.4 g of the DTPA-mono-2-(N-tert-butoxycarbonylamino)ethylamide obtained above, and, after stirring the mixture for 3 hours, the reaction mixture was added dropwise to diethyl ether to precipitate the reaction product. The reaction product precipitated was collected by suction filtration, and was dried under a reduced pressure, to obtain 20.2 g of DTPA-mono-2-aminoethylamide as the objective compound.

<3> Covalent Bond Between Block Copolymer and Linker Molecule-Bonded Chelating Agent, and Coordination of Paramagnetic Ion A polymer in which the block copolymer having a reactive group is the block copolymer obtained in <1> above and the linker molecule-bonded chelating agent is the DTPA-mono-2-aminoethylamide obtained in <2> above and the paramagnetic ion is gadolinium(III), was synthesized.

To a solution prepared by dissolving 5.32 g of the block copolymer obtained in <1> above in 160 ml of anhydrous DMF, a solution obtained by dissolving 1.78 g of the DTPA-mono-2-aminoethylamide obtained in <2> above in 40 ml of anhydrous DMF was added dropwise at room temperature, followed by stirring at 80° C. for 18 hours. Subsequently, to the reaction mixture was added 20.0 ml of 0.1 M DMF solution of gadolinium chloride hexahydrate (Gadolinium Chloride Hexahydrate, 99.9%, produced by Wako Pure Chemical Industries, Ltd.), followed by stirring further at the above-mentioned temperature for 1 hour. The reaction mixture was added dropwise to diethyl ether to precipitate the reaction product, and the product was collected by suction filtration, and dried under a reduced pressure, to obtain 6.17 g of Polymer 1.

<Evaluation>

<4> Formation of Cast Film

A 2 wt % solution of Polymer 1 obtained in Example 1 was prepared by using methanol (produced by Kokusan Chemical Co., Ltd.) or chloroform (produced by Kanto Chemical Co., Ltd.) as a solvent, 5 ml of the solution was developed in a polytetrafluoroethylene-made Petri dish (φ30 mm) and dried, to form a cast film having a thickness of 50 to 100 μm (Film 1).

<5> Determination of Gadolinium(III) Contained in Cast Film

Film 1 was placed in a nylon bag (255 mesh, 10×20 cm), was washed with running water for 3 hours, and dried under a reduced pressure. A weighed amount of the thus washed film was placed in a porcelain crucible, 500 μl of nitric acid (atomic absorption grade, produced by Kanto Chemical Co., Ltd.) was added thereto, then the film was carbonized by heating on a 300° C. hot plate until generation of while smoke ceased, and was ashed in an electric muffle furnace at 500° C. After cooling, the ash thus obtained was dissolved in 100 μl of nitric acid, and distilled water is added thereto to a total volume of 10 ml. Determination of gadolinium(III) was conducted by ICP (inductively coupled plasma) emission spectrometry (ICPS-8000, produced by Shimadzu Corp., measurement wavelength: 342.247 nm), and the amount of gadolinium contained per unit weight of the polymer (mg/g) was calculated, the result being shown in Table 1 below.

<6> Evaluation of Surface Lubricity by Use of Sheet-Formed Specimen

Polyurethane pellets (PANDEX T5000, produced by Dainippon Ink And Chemicals, Inc.) were heat pressed at 180° C. and 20 MPa for 3 minutes by use of a press (Desktop-type Test Press, produced by Test Sangyo Co., Ltd.), followed by rapid cooling, to produce a polyurethane sheet having a thickness of 1 mm. The sheet was immersed in a 4.5 wt % DMF solution of Polymer 1, immediately followed by pulling it up at a velocity of 50 mm/min, and was dried at 100° C. for 10 hours, to form a layer of Polymer 1 on the surface of the sheet. Subsequently, the sheet was washed with running water for 3 hours, and was dried at 50° C. for 1 hour, to obtain Sheet 1. Thereafter, frictional resistance on the sheet surface was measured, as shown in FIG. 2.

<7> Evaluation of Surface Lubricity by Use of Wire-Formed Specimen

A guide wire (diameter: 0.035 inch, produced by Terumo Corp.) was immersed in a 4.5 wt % DMF solution of Polymer 1, immediately followed by pulling it up at a velocity of 50 mm/min, and was dried at 100° C. for 10 hours, to form a polymer layer on the surface of the guide wire. Subsequently, the guide wire was washed with running water for 3 hours, and dried at 50° C. for 1 hour, to obtain Wire 1. Thereafter, frictional resistance on Wire 1 was measured, as shown in FIG. 3.

<8> Preparation of Tubular Specimen

A polyurethane tube (1.55 mm in outer diameter and 1.10 mm in inner diameter, produced by Nirei Industry Co., Ltd.) was immersed in 10 wt % DMF solution of Polymer 1, immediately followed by pulling it up at a velocity of 100 mm/min, and was dried at 80° C. for 3 hours, to form a polymer layer on the surfaces of the tube. Subsequently, the tube was washed with running water for 3 hours, and was dried at 50° C. for 3 hours, to obtain Tube 1.

<9> Evaluation of MRI Visibility

Film 1 was cut into a circular piece φ8 mm, which was washed with distilled water, was then placed in a polystyrene bottle together with 5 ml of a physiological saline (Terumo Seishoku, produced by Terumo Corp.), and was subjected to MRI imaging. The MRI apparatus used was APERTO (magnetostatic field intensity: 0.4 T, produced by Hitachi Medical Corp.), and the reception RF coil used was QD Head Coil. As for imaging conditions, SE (Condition 1) and GE (RSSG) (Condition 2) sequences were used. The visibility of the cast film was evaluated on the MRI image.

Similarly, the visibility of the cast film was evaluated also by using Sigma EXITE Twin Speed Ver. 11 (static magnetic field strength: 1.5 T, produced by GE Healthcare) as an MRI apparatus, Standard Head Coil (Birdcage) as a reception RF coil, and using SE (Condition 3) and GE (SPGR) (Condition 4) sequences as imaging conditions. The results are shown in Table 1.

In addition, Tube 1 prepared above was immersed in a physiological saline (Terumo Seishoku, produced by Terumo Corp.), and MRI visibility was evaluated by MRI imaging. Incidentally, the same MRI apparatus and imaging conditions as those for the cast film were used here. The results are shown in Table 1.

For Sheet 1 and Wire 1 formed above, MRI visibility was evaluated before and after the surface lubricity test. Incidentally, the same MRI apparatus and imaging conditions as those for the cast film were used here. The results are shown in Table 1.

Example 2

Film 2, Sheet 2, Wire 2, and Tube 2 were obtained in the same manner as in Example 1, except that the amount of DTPA-mono-2-aminoethylamide added in <3> of Example 1 was changed to 0.35 g and the amount of the 0.1 M DMF solution of gadolinium chloride hexahydrate added was changed to 4 ml.

Example 3

Film 3, Sheet 3, Wire 3, and Tube 3 were obtained in the same manner as in Example 1, except that the amount of DTPA-mono-2-aminoethylamide added in <3> of Example 1 was changed to 0.036 g, and the amount of the 0.1 M DMF solution of gadolinium chloride hexahydrate added was changed to 0.40 ml.

Example 4

DTPA-mono-6-aminohexylamide in which the linker molecule as that in <2> of Example 1 is 1,6-diaminohexane, was synthesized.

After 10.7 g (30 mM) of diethylenetriaminepentaacetic acid dianhydride (DTPAda, produced by Aldrich) was added to 150 ml of anhydrous dimethylformamide (anhydrous DMF, produced by Wako Pure Chemical Industries, Ltd.) and the admixture was heated at 80° C. to effect dissolution, 0.54 ml (30 mM) of distilled water was added dropwise to the solution, followed by stirring further for 1 hour. To the thus obtained solution, a solution prepared by dissolving 6.49 g (30 mM) of N-(tert-butoxycarbonyl)-1,6-diaminohexane (produced by Tokyo Chemical Industries Co., Ltd.) in 36 ml of anhydrous DMF was added dropwise, followed by stirring further for 2 hours at the above-mentioned temperature. The reaction mixture was added dropwise to diethyl ether (produced by Kokusan Chemical Co., Ltd.) to precipitate the reaction product, and the product was collected by suction filtration, and was dried under a reduced pressure, to obtain 16.0 g of a white powder. The powder was isolated and purified by chromatography using chromatography-grade (ChromatorexODS DM1020T, produced by Fuji Silysia Chemical Ltd.) and using water/acetonitrile (produced by Kanto Chemical Co., Ltd.) mixed solvent (6/4, v/v) as a developing solvent, to obtain DTPA-mono-6-(N-tert-butoxycarbonylamino)hexylamide.

Subsequently, 25 ml of trifluoroacetic acid (produced by Wako Pure Chemical Industries, Ltd.) was added to 2.41 g of the DTPA-mono-6-(N-tert-butoxycarbonylamino)hexylamide obtained above, and, after stirring the mixture for 3 hours, the reaction mixture was added dropwise to diethyl ether to precipitate the reaction product. The reaction product precipitated was collected by suction filtration, and was dried under a reduced pressure, to obtain 2.60 g of DTPA-mono-6-aminohexylamide as the objective compound.

Using the DTPA-mono-6-aminohexylamide, a polymer in which the block copolymer having a reactive group in <3> of Example 1 is the block copolymer obtained in <1> of Example 1 and the linker molecule-bonded chelating agent is DTPA-mono-6-aminohexylamide and the paramagnetic ion is gadolinium(III), was synthesized.

To a solution prepared by dissolving 0.67 g of the block copolymer obtained in <1> of Example 1 in 20 ml of anhydrous DMF, a solution prepared by dissolving 0.47 g of the DTPA-mono-6-aminohexylamide obtained above in 5 ml of anhydrous DMF was added dropwise at room temperature, followed by stirring at 80° C. for 18 hours. Subsequently, to the reaction mixture was added 5.0 ml of 0.1 M DMF solution of gadolinium chloride hexahydrate (Gadolinium Chloride Hexahydrate, 99.9%, produced by Wako Pure Chemical Industries, Ltd.), followed by stirring further at the above-mentioned temperature for 1 hour. The reaction mixture was added dropwise to diethyl ether to precipitate the reaction product, and the product was collected by suction filtration, and dried under a reduced pressure, to obtain 0.95 g of Polymer 4.

Film 4, Sheet 4, Wire 4, and Tube 4 were obtained by use of the thus obtained Polymer 4 in the same manner as in Example 1, except that the concentration of solution of Polymer 4 was set to 10 wt %, the pulling-up velocity was set to 50 mm/min, and the drying conditions were set to 80° C. and 3 hours, in carrying out the evaluation of surface lubricity by use of a sheet-formed specimen in <6>, the evaluation of surface lubricity by use of a wire-formed specimen in <7>, and the preparation of a tubular specimen in <8> in Example 1.

Example 5

Film 5, Sheet 5, Wire 5, and Tube 5 were obtained in the same manner as in Example 4, except that the amount of DTPA-mono-6-aminohexylamide added in Example 4 was changed to 0.36 g, and the amount of the 0.1 M DMF solution of gadolinium chloride hexahydrate added was changed to 3.75 ml.

Example 6

Film 6, Sheet 6, Wire 6, and Tube 6 were obtained in the same manner as in Example 4, except that the amount of DTPA-mono-6-aminohexylamide added in Example 4 was changed to 0.23 g, and the amount of the 0.1 M DMF solution of gadolinium chloride hexahydrate added was changed to 2.50 ml.

Example 7

DTPA-mono-12-aminododecylamide in which the linker molecule as that in <2> of Example 1 is 1,12-diaminododecane, was synthesized.

After 21.4 g (60 mM) of diethylenetriaminepentaacetic acid dianhydride (DTPAda, produced by Aldrich) was added to ml of anhydrous dimethylformamide (Anhydrous DMF, produced by Wako Pure Chemical Industries, Ltd.) and the admixture was heated at 80° C. to effect dissolution, 1.08 ml mM) of distilled water was added dropwise to the solution, followed by stirring further for 1 hour. To the thus obtained solution, a solution of 18.1 g (60 mM) of N-(tert-butoxycarbonyl)-1,12-diaminododecane (synthesized in the same manner as C. Dardonville et al., Bioorg. Med. Chem. 14 (2006), 6570-6580) in 60 ml of anhydrous DMF was added dropwise, followed by stirring further for 2 hours at the above-mentioned temperature. The reaction mixture was added dropwise to diethyl ether (produced by Kokusan Chemical Co., Ltd.) to precipitate the reaction product, and the product was collected by suction filtration, and was dried under a reduced pressure, to obtain 29.2 g of a white powder. The powder was recrystallized by use of water/acetonitrile (produced by Kanto Chemical Co., Ltd.) mixed solvent (6/4, v/v), to obtain DTPA-mono-12-(N-tert-butoxycarbonylamino)dodecylamide.

Subsequently, 45 ml of trifluoroacetic acid (produced by Wako Pure Chemical Industries, Ltd.) was added to 4.37 g of the DTPA-mono-12-(N-tert-butoxycarbonylamino)dodecylamide obtained above, and, after stirring the mixture for 3 hours, the reaction mixture was added dropwise to diethyl ether to precipitate the reaction product. The reaction product precipitated was collected by suction filtration, and was dried under a reduced pressure, to obtain 4.76 g of DTPA-mono-12-aminododecylamide as the objective compound.

Using the DTPA-mono-12-aminododecylamide, a copolymer in which the block copolymer having a reactive group in <3> of Example 1 is the block copolymer obtained in <1> of Example 1 and the linker molecule-bonded chelating agent is DTPA-mono-12-aminododecylamide and the paramagnetic ion is gadolinium(III), was synthesized.

To a solution prepared by dissolving 1.33 g of the block copolymer obtained in <1> of Example 1 in 50 ml of anhydrous DMF, a solution prepared by dissolving 0.258 g of the DTPA-mono-12-aminododecylamide obtained above in 4 ml of anhydrous DMF was added dropwise at room temperature, followed by stirring at 120° C. for 6 hours. Subsequently, to the reaction mixture was added 2.50 ml of 0.1 M DMF solution of gadolinium chloride hexahydrate (Gadolinium Chloride Hexahydrate, 99.9%, produced by Wako Pure Chemical Industries, Ltd.), followed by stirring further at the above-mentioned temperature for 1 hour. The reaction mixture was added dropwise to diethyl ether to precipitate the reaction product, and the product was collected by suction filtration, and dried under a reduced pressure, to obtain 1.31 g of Polymer 7.

Film 7, Sheet 7, Wire 7, and Tube 7 were obtained by use of the thus obtained Polymer 7 in the same manner as in Example 1, except that the concentration of solution of Polymer 7 was set to 10 wt %, the pulling-up velocity was set to 50 mm/min, and the drying conditions were set to 130° C. and 1 hour, in carrying out the evaluation of surface lubricity by use of a sheet-formed specimen in <6>, the evaluation of surface lubricity by use of a wire-formed specimen in <7>, and the preparation of a tubular specimen in <8> in Example 1.

Example 8

Film 8, Sheet 8, Wire 8, and Tube 8 were obtained in the same manner as in Example 7, except that the amount of the block copolymer used in Example 7 was changed to 0.67 g, the amount of DTPA-mono-12-aminododecylamide added was changed to 0.077 g, and the amount of the 0.1 M DMF solution of gadolinium chloride hexahydrate added was changed to 0.75 ml.

Example 9

DTPA-mono-4-(aminomethyl)benzylamide in which the linker molecule as that in <2> of Example 1 is p-xylenediamine, was synthesized.

After 22.2 g (62 mM) of diethylenetriaminepentaacetic acid dianhydride (DTPAda, produced by Aldrich) was added to 310 ml of anhydrous dimethylformamide (Anhydrous DMF, produced by Wako Pure Chemical Industries, Ltd.) and the admixture was heated at 80° C. to effect dissolution, 1.12 ml (62 mM) of distilled water was added dropwise to the solution, followed by stirring further for 1 hour. To the thus obtained solution, a solution of 14.6 g (62 mM) of N-(tert-butoxycarbonyl)-p-xylylenediamine (synthesized in the same manner as C. Dardonville et al., Bioorg. Med. Chem., 14 (2006), 6570-6580) in 62 ml of anhydrous DMF was added dropwise, followed by stirring further for 2 hours at the above-mentioned temperature. The reaction mixture was added dropwise to diethyl ether (produced by Kokusan Chemical Co., Ltd.) to precipitate the reaction product, and the product was collected by suction filtration, and was dried under a reduced pressure, to obtain 35.3 g of a white powder. The powder was isolated and purified by chromatography using chromatography-grade (ChromatorexODS DM1020T, produced by Fuji Silysia Chemical Ltd.) and using water/acetonitrile (produced by Kanto Chemical Co., Ltd.) mixed solvent (8/2, v/v) as a developing solvent, to obtain DTPA-mono-4-(N-tert-butoxycarbonylaminomethyl)benzylamide.

Subsequently, 100 ml of trifluoroacetic acid (produced by Wako Pure Chemical Industries, Ltd.) was added to 9.51 g of the DTPA-mono-4-(N-tert-butoxycabonylaminomethyl) benzylamide obtained above, and, after stirring the mixture for 3 hours, the reaction mixture was added dropwise to diethyl ether to precipitate the reaction product. The reaction product precipitated was collected by suction filtration, and was dried under a reduced pressure, to obtain 10.60 g of DTPA-mono-4-(aminomethyl)benzylamide as the objective compound.

Using the DTPA-mono-4-(aminomethyl)benzylamide, a polymer in which the block copolymer having a reactive group in <3> of Example 1 is the block copolymer obtained in <1> of Example 1 and the linker molecule-bonded chelating agent is DTPA-mono-4-(aminomethyl)benzylamide and the paramagnetic ion is gadolinium(III), was synthesized.

To a solution prepared by dissolving 0.67 g of the block copolymer obtained in <1> of Example 1 in 25 ml of anhydrous DMF, a solution prepared by dissolving 0.048 g of the DTPA-mono-4-(aminomethyl)benzylamide obtained above in 2 ml of anhydrous DMF was added dropwise at room temperature, followed by stirring at 120° C. for 6 hours. Subsequently, to the reaction mixture was added 0.50 ml of 0.1 M DMF solution of gadolinium chloride hexahydrate (Gadolinium Chloride Hexahydrate, 99.9%, produced by Wako Pure Chemical Industries, Ltd.), followed by stirring further at the above-mentioned temperature for 1 hour. The reaction mixture was added dropwise to diethyl ether to precipitate the reaction product, and the product was collected by suction filtration, and dried under a reduced pressure, to obtain 0.56 g of Polymer 9.

Film 9, Sheet 9, Wire 9, and Tube 9 were obtained by use of Polymer 9, in the same manner as in Example 7.

Example 10

DTPA-mono-(4-(aminomethyl)cyclohexyl)methylamide in which the linker molecule as that in <2> of Example 1 is cyclohexan-1,4-diyldimethaneamine, was synthesized.

After 20.7 g (58 mM) of diethylenetriaminepentaacetic acid dianhydride (DTPAda, produced by Aldrich) was added to 290 ml of anhydrous dimethylformamide (Anhydrous DMF, produced by Wako Pure Chemical Industries, Ltd.) and the admixture was heated at 80° C. to effect dissolution, 1.04 ml (58 mM) of distilled water was added dropwise to the solution, followed by stirring further for 1 hour. To the thus obtained solution, a solution of 13.9 g (57 mM) of N-(tert-butoxycarbonyl)-cyclohexan-1,4-diyldimethaneamine (synthesized in the same manner as C. Dardonville et al., Bioorg. Med. Chem., 14 (2006), 6570-6580) in 62 ml of anhydrous DMF was added dropwise, followed by stirring further for 2 hours at the above-mentioned temperature. The reaction mixture was added dropwise to diethyl ether (produced by Kokusan Chemical Co., Ltd.) to precipitate the reaction product, and the product was collected by suction filtration, and was dried under a reduced pressure, to obtain 39.1 g of a white powder. The powder was isolated and purified by chromatography using chromagography-grade (ChromatorexODS DM1020T, produced by Fuji Silysia Chemical Ltd.) and using water/acetonitrile (produced by Kanto Chemical Co., Ltd.) mixed solvent (8/2, v/v) as a developing solvent, to obtain DTPA-mono-(4-(N-tert-butoxycarbonylaminomethyl)cyclohexyl)methylamide.

Subsequently, 95 ml of trifluoroacetic acid (produced by Wako Pure Chemical Industries, Ltd.) was added to 9.22 g of the DTPA-mono-(4-(N-tert-butoxycarbonylaminomethyl)cyclohexyl)methylamide obtained above, and, after stirring the mixture for 3 hours, the reaction mixture was added dropwise to diethyl ether to precipitate the reaction product. The reaction product precipitated was collected by suction filtration, and was dried under a reduced pressure, to obtain 11.0 g of DTPA-mono-(4-(aminomethyl)cyclohexyl)methylamide as the objective compound.

Using the DTPA-mono-(4-(aminomethyl)cyclohexyl)methylamide, a polymer in which the block copolymer having a reactive group in <3> of Example 1 is the block copolymer obtained in <1> of Example 1 and the linker molecule-bonded chelating agent is DTPA-mono-(4-(aminomethyl)cyclohexyl)methylamide and the paramagnetic ion is gadolinium(III), was synthesized.

To a solution prepared by dissolving 0.67 g of the block copolymer obtained in <1> of Example 1 in 25 ml of anhydrous DMF, a solution prepared by dissolving 0.049 g of the DTPA-mono-(4-(aminomethyl)cyclohexyl)methylamide obtained above in 2 ml of anhydrous DMF was added dropwise at room temperature, followed by stirring at 120° C. for 6 hours. Subsequently, to the reaction mixture was added 0.50 ml of 0.1 M DMF solution of gadolinium chloride hexahydrate (Gadolinium Chloride Hexahydrate, 99.9%, produced by Wako Pure Chemical Industries, Ltd.), followed by stirring further at the above-mentioned temperature for 1 hour. The reaction mixture was added dropwise to diethyl ether to precipitate the reaction product, and the product was collected by suction filtration, and dried under a reduced pressure, to obtain 0.53 g of Polymer 10.

Film 10, Sheet 10, Wire 10, and Tube 10 were obtained by use of Polymer 10, in the same manner as in Example 7.

Example 11

Film 11, Sheet 11, Wire 11, and Tube 11 were obtained in the same manner as in Example 7, except that DOTA (produced by Aldrich) was used as a chelating agent corresponding to that used in Example 7.

Example 12

Film 12, Sheet 12, Wire 12, and Tube 12 were obtained in the same manner as in Example 7, except that p-aminobenzyl-diethylenetriaminepentaacetic acid (p-NH2-Bz-DTPA, produced by Macrocyclics) was used as a linker molecule-bonded chelating agent corresponding to that used in <3> of Example 1.

Example 13

Film 13, Sheet 13, Wire 13, and Tube 13 were obtained in the same manner as in Example 7, except that vinylpyrrolidone was used in place of DMAA used in <1> of Example 1, and 2-p-aminobenzyl-1,4,7,10-tetraazacyclododecane-1,4,7,10-tetraacetic acid (p-NH2-Bz-DOTA, produced by Macrocyclics) was used as a linker molecule-bonded chelating agent corresponding to that used in <3> of Example 1.

Example 14

Film 14, Sheet 14, Wire 14, and Tube 14 were obtained in the same manner as in Example 7, except that polymerization was carried out by simultaneously adding HEMA-DTPA, obtained by bonding DTPA to 2-hydroxyethyl methacrylate (HEMA, produced by Wako Pure Chemical Industries, Ltd.), in the step of adding DMAA in <1> of Example 1 and that DTPA-mono-2-aminoethylamide was not used.

Comparative Example 1

Film 15, Sheet 15, Wire 15, and Tube 15 were obtained in the same manner as in Example 1, except that the block copolymer obtained in <1> of Example 1 was not subjected to either of the operations of <2> and <3> of Example 1.

Comparative Example 2

A polymer was prepared by using gelatin in place of <1> of Example 1.

In 20 ml of distilled water, 0.6 g of gelatin (produced by Wako Pure Chemical Industries, Ltd.) was dissolved at 60° C. over 1 hour. Next, the gelatin solution kept at or above 40° C. and one-third at a time of 0.5 g of diethylenetriaminepentaacetic acid dianhydride were added to 20 ml of distilled water at 35° C. with stirring. During this operation, the pH of the solution was kept at 10 by use of 6 N aqueous sodium hydroxide solution (Sodium Hydroxide, produced by Kanto Chemical Co., Ltd.). After the addition of all the reagents, the solution was stirred further for 4 hours. After the reaction was over, the pH was adjusted to 6.5 by use of 1 N nitric acid (Nitric Acid, produced by Kanto Chemical Co., Ltd.). To 100 ml of distilled water at 60° C., there were added 2.5 g of the reaction mixture obtained above, 2.5 g of DTPA (produced by Dojindo Laboratories) and 20 g of gelatin, and dissolution was allowed with stirring for 1 hour, to obtain Polymer 16.

The solution of Polymer 16, in an amount of 5 ml, was developed in a polytetrafluoroethylene-made Petri dish and dried, to form a cast film (Film 16). In addition, while keeping Polymer 16 at 35° C., the polyurethane sheet and the guide wire and the tube prepared in Example 1 were immersed in the polymer and pulled out at a velocity of 50 mm/min, followed by air drying to room temperature, to form layers of Polymer 16 on the surfaces of the sheet, the guide wire, and the tube. After several minutes, the cast film, the sheet, the guide wire, and the tube were immersed in 300 ml of 0.5% glutaraldehyde (25% Glutaraldehyde Solution, produced by Wako Pure Chemical Industries, Ltd.) for 2 hours, to crosslink gelatin. The cast film, the sheet, the guide wire, and the tube were washed with distilled water, and were immersed further in distilled water for 2 hours. Subsequently, they were immersed for 8 to 10 hours in a solution prepared by dissolving 5.1 g of gadolinium chloride hexahydrate in 900 ml of distilled water, whereby gadolinium(III) was coordinated with DTPA. The cast film, the sheet, the guide wire, and the tube were washed with distilled water, and were immersed further in distilled water for 8 to 10 hours, followed by air drying, to obtain Film 16, Sheet 16, Wire 16, and Tube 16.

Films 2 to 16, Sheets 2 to 16, Wires 2 to 16, and Tubes 2 to 16 obtained as above were evaluated in the same manner as in Example 1.

Comparative Example 3

Using the polymer-uncoated polyurethane sheet (Sheet 17) and the polymer-uncoated guide wire (Wire 17) and the polymer-uncoated tube (Tube 17) which were prepared in Example 1, evaluation was performed in the same manner as in Example 1.

Evaluation results of Films 1 to 16, Sheets 1 to 17, Wires 1 to 17, and Tubes 1 to 17 obtained in Examples 1 to 14 and Comparative Examples 1 to 3 above are shown in Table 1. Here, in the evaluation of MRI visibility, those which were visible in MRI images before and after the surface lubricity test were marked "o," whereas those which were not visible were marked "x." In the evaluation of surface lubricity, a lower final frictional resistance represents higher lubricity, and a smaller change in frictional resistance means that the polymer was bound to the substrate surface more stably and, therefore, better in peel resistance. It is to be noted here that in the cases of Sheet 16 (Comparative Example 2) and Sheet 17 (Comparative Example 3), the frictional resistance was so large that the repeating motion of the cylindrical brass weight became impossible before the motion was repeated 100 times; therefore, the final frictional resistance was expressed as "100 or more," and the Δ frictional resistance was evaluated as unmeasurable and expressed as "-" in the table. Besides, in Comparative Example 3, the film specimen was absent and, therefore, expressed as "none."

TABLE 1

|  | Amount of Gadolinium (III) [mg/g] | Film MRI Visibility Conditions 1-4 | Tube MRI Visibility Conditions 1-4 | Sheet Final Frictional Resistance [N] | Sheet Δ Frictional Resistance [N] | MRI Visibility Conditions 1-4 Before Test | MRI Visibility Conditions 1-4 After Test | Wire Final Frictional Resistance [N] | Wire Δ Frictional Resistance [N] | MRI Visibility (Conditions 1-4) Before Test | MRI Visibility (Conditions 1-4) Test Test |
|---|---|---|---|---|---|---|---|---|---|---|---|
| Example 1 | 1.0 | o | o | 20 | 2 | o | o | 0.1 | 0.01 or less | o | o |
| Example 2 | 0.3 | o | o | 20 | 1 | o | o | 0.2 | 0.01 or less | o | o |
| Example 3 | 0.1 | o | o | 21 | 3 | o | o | 0.2 | 0.01 or less | o | o |
| Example 4 | 1.0 | o | o | 20 | 2 | o | o | 0.1 | 0.01 or less | o | o |
| Example 5 | 2.0 | o | o | 20 | 3 | o | o | 0.2 | 0.01 or less | o | o |
| Example 6 | 2.1 | o | o | 21 | 2 | o | o | 0.2 | 0.01 or less | o | o |
| Example 7 | 4.8 | o | o | 20 | 1 | o | o | 0.1 | 0.01 or less | o | o |
| Example 8 | 3.5 | o | o | 21 | 2 | o | o | 0.1 | 0.01 or less | o | o |
| Example 9 | 2.7 | o | o | 22 | 4 | o | o | 0.2 | 0.01 or less | o | o |
| Example 10 | 1.6 | o | o | 20 | 2 | o | o | 0.2 | 0.01 or less | o | o |
| Example 11 | 1.0 | o | o | 21 | 4 | o | o | 0.1 | 0.01 or less | o | o |
| Example 12 | 0.9 | o | o | 20 | 2 | o | o | 0.2 | 0.01 or less | o | o |
| Example 13 | 0.9 | o | o | 21 | 3 | o | o | 0.1 | 0.01 or less | o | o |
| Example 14 | 1.0 | o | o | 21 | 2 | o | o | 0.1 | 0.01 or less | o | o |
| Comp. Ex. 1 | 0.0 | x | x | 21 | 4 | x | x | 0.2 | 0.01 or less | x | x |
| Comp. Ex. 2 | 4.5 | o | o | 100 or more | — | o | x | 1.0 | 0.4 | o | x |
| Comp. Ex. 3 | none | none | x | 100 or more | — | x | x | 0.9 | 0.01 or less | x | x |

INDUSTRIAL APPLICABILITY

As has been described above, the coating layers on the films, sheets and wires according to the present invention shown in Examples 1 to 14 were swelled immediately upon immersion in physiological saline, showed high signals in MRI images, and were slippery to the touch, by which they were verified to develop MRI visibility and surface lubricity. Further, the coating layers composed of the polymers according to the present invention were confirmed to be superior in peel resistance, as compared with the coating layers obtained in the comparative examples.

The invention claimed is:
1. A medical apparatus, comprising a substrate surface that is coated with a coating formed from a block copolymer comprising a moiety having a reactive group which is an epoxy group; and a moiety for developing lubricity comprising a hydrophilic monomer or a repetition of said monomer,
wherein a substance for shortening relaxation time of a nuclear species capable of being detected by magnetic resonance is chemically bound to an epoxy group of the block copolymer,
wherein the block copolymer is directly attached to the substrate surface of the medical apparatus, wherein the molar ratio of the moiety having a reactive group to the moiety for developing lubricity is 1:3 to 1:19, wherein said copolymer, when wetted, develops surface lubricity and MRI visibility, wherein either one of said moieties and said substance for shortening said relaxation time are covalently bound to each other either directly or through a linker molecule, and wherein said linker molecule is at least one selected from the group consisting of a diamine, amino-alcohol, dialkylenetriamine, aminocarboxylic acid, lactam, diol, hydroxycarboxylic acid, dicarboxylic acid, diisocyanate, diisothiocyanate, aminoisocyanate, aminoisothiocyanate, hydroxylisocyanate, hydroxylisothiocyanate, carboxylisocyanate, and carboxylisothiocyanate.

2. The block copolymer according to claim 1, wherein said substance for shortening the relaxation time of a nuclear species capable of being detected by magnetic resonance includes an ion or particle which is paramagnetic or superparamagnetic.

3. The block copolymer according to claim 1, wherein said hydrophilic monomer is at least one selected from the group consisting of: acrylamide and its derivatives; acrylic acid, methacrylic acid and their derivatives; maleic anhydride, maleic acid and their derivatives; and vinylpyrrolidone.

4. The block copolymer according to claim 1, wherein said moiety having a reactive group comprises a monomer having said reactive group in its molecule or a repetition of said monomer.

5. The block copolymer according to claim 1, wherein said copolymer is a block copolymer including a block comprising a monomer having a reactive group in its molecule, and a block comprising a hydrophilic monomer.

6. The medical apparatus according to claim 1, wherein said medical apparatus, when wetted, develops surface lubricity and MRI visibility.

7. A medical apparatus, comprising a substrate surface that is coated with a coating formed from a block copolymer comprising a moiety having a reactive group which is an epoxy group, and a moiety for developing lubricity comprising a hydrophilic monomer or a repetition of said monomer, wherein a substance for shortening relaxation time of a nuclear species capable of being detected by magnetic resonance is chemically bound to the moiety for developing lubricity, wherein the block copolymer is directly attached to the substrate surface of the medical apparatus, wherein the molar ratio of the moiety having a reactive group to the moiety for developing lubricity is 1:3 to 1:19;

wherein said copolymer, when wetted, develops surface lubricity and MRI visibility, wherein either one of said moieties and said substance for shortening said relaxation time are covalently bound to each other either directly or through a linker molecule, and wherein said linker molecule is at least one selected from the group consisting of a diamine, amino-alcohol, dialkylenetriamine, aminocarboxylic acid, lactam, diol, hydroxycarboxylic acid, dicarboxylic acid, diisocyanate, diisothiocyanate, aminoisocyanate, aminoisothiocyanate, hydroxylisocyanate, hydroxylisothiocyanate, carboxylisocyanate, and carboxylisothiocyanate.

8. The medical apparatus according to claim 1, wherein a part of the epoxy groups is covalently bonded to the substrate surface.

9. A medical apparatus wherein a substrate surface is coated with the block copolymer according to claim 7, wherein a part of the epoxy groups is covalently bonded to the substrate surface.

10. The medical apparatus according to claim 1, wherein either one of said moieties and said substance for shortening said relaxation time are covalently bound to each other through a linker molecule.

11. The medical apparatus according to claim 7, wherein either one of said moieties and said substance for shortening said relaxation time are covalently bound to each other through a linker molecule.

12. A medical apparatus, comprising a substrate surface that is coated with a coating formed from a block copolymer comprising a moiety having a reactive group which is an epoxy group; and a moiety for developing lubricity comprising a hydrophilic monomer or a repetition of said monomer, wherein a substance for shortening relaxation time of a nuclear species capable of being detected by magnetic resonance is chemically bound to an epoxy group of the block copolymer, wherein the block copolymer is directly attached to the substrate surface of the medical apparatus, wherein said copolymer, when wetted, develops surface lubricity and MRI visibility, wherein either one of said moieties and said substance for shortening said relaxation time are covalently bound to each other either directly or through a linker molecule, and wherein said linker molecule is at least one selected from the group consisting of a diamine, amino-alcohol, dialkylenetriamine, aminocarboxylic acid, lactam, diol, hydroxycarboxylic acid, dicarboxylic acid, diisocyanate, diisothiocyanate, aminoisocyanate, aminoisothiocyanate, hydroxylisocyanate, hydroxylisothiocyanate, carboxylisocyanate, and carboxylisothiocyanate.

13. A medical apparatus, comprising a substrate surface that is coated with a coating formed from a block copolymer comprising a moiety having a reactive group which is an epoxy group, and a moiety for developing lubricity comprising a hydrophilic monomer or a repetition of said monomer, wherein a substance for shortening relaxation time of a nuclear species capable of being detected by magnetic resonance is chemically bound to the moiety for developing lubricity, wherein the block copolymer is directly attached to the substrate surface of the medical apparatus, wherein said copolymer, when wetted, develops surface lubricity and MRI visibility, wherein either one of said moieties and said substance for shortening said relaxation time are covalently bound to each other either directly or through a linker molecule, and wherein said linker molecule is at least one selected from the group consisting of a diamine, amino-alcohol, dialkylenetriamine, aminocarboxylic acid, lactam, diol, hydroxycarboxylic acid, dicarboxylic acid, diisocyanate, diisothiocyanate, aminoisocyanate, aminoisothiocyanate, hydroxylisocyanate, hydroxylisothiocyanate, carboxylisocyanate, and carboxylisothiocyanate.

* * * * *